(12) United States Patent
Dave et al.

(10) Patent No.: US 10,278,605 B2
(45) Date of Patent: May 7, 2019

(54) METHODS AND DEVICES FOR SAMPLE CHARACTERIZATION

(71) Applicant: THE METHODIST HOSPITAL SYSTEM, Houston, TX (US)

(72) Inventors: Amish S. Dave, Houston, TX (US); Miguel Valderrábano, Houston, TX (US)

(73) Assignee: The Methodist Hospital System, Houston, TX (US)

( * ) Notice: Subject to any disclaimer, the term of this patent is extended or adjusted under 35 U.S.C. 154(b) by 0 days.

(21) Appl. No.: 15/559,954

(22) PCT Filed: Mar. 23, 2016

(86) PCT No.: PCT/US2016/023731
§ 371 (c)(1),
(2) Date: Sep. 20, 2017

(87) PCT Pub. No.: WO2016/154280
PCT Pub. Date: Sep. 29, 2016

(65) Prior Publication Data
US 2018/0070846 A1    Mar. 15, 2018

Related U.S. Application Data

(60) Provisional application No. 62/136,683, filed on Mar. 23, 2015.

(51) Int. Cl.
*A61B 5/00* (2006.01)
*A61B 5/04* (2006.01)
(Continued)

(52) U.S. Cl.
CPC ............ *A61B 5/0452* (2013.01); *A61B 5/046* (2013.01); *A61B 5/04012* (2013.01);
(Continued)

(58) Field of Classification Search
CPC ........................... A61B 5/7275; A61B 5/7282
(Continued)

(56) References Cited

U.S. PATENT DOCUMENTS

| | | |
|---|---|---|
| 5,868,680 A | 2/1999 | Steiner et al. |
| 6,256,535 B1 | 7/2001 | Province et al. |

(Continued)

FOREIGN PATENT DOCUMENTS

| | | |
|---|---|---|
| WO | 2010042826 | 4/2010 |
| WO | 2011127209 | 10/2011 |

(Continued)

OTHER PUBLICATIONS

Umapathy et al. Phase mapping of cardiac fibrillation. Circ Arrythm Electrophysiol 2010, 3, 105-114.
(Continued)

*Primary Examiner* — Amanda K Hulbert
*Assistant Examiner* — Philip C Edwards
(74) *Attorney, Agent, or Firm* — Meunier Carlin & Curfman LLC

(57) ABSTRACT

Provided herein are methods and devices for the detection, quantification, and/or monitoring of characteristics in samples. The disclosed methods and devices can be used, for example, to identify the presence and location of atrial fibrillation indicators with high spatial resolution. The disclosed methods and devices can even be used to identify the presence and location of atrial fibrillation indicators using non-simultaneously collected data.

39 Claims, 2 Drawing Sheets

(51) Int. Cl.
*A61B 18/00* (2006.01)
*A61B 18/14* (2006.01)
*A61B 5/042* (2006.01)
*A61B 5/046* (2006.01)
*G01R 19/25* (2006.01)
*G01R 23/02* (2006.01)
*G01R 25/00* (2006.01)
*A61B 5/0452* (2006.01)

(52) U.S. Cl.
CPC .......... *A61B 5/0422* (2013.01); *A61B 5/6852* (2013.01); *G01R 19/2503* (2013.01); *G01R 23/02* (2013.01); *G01R 25/005* (2013.01); *A61B 18/1492* (2013.01); *A61B 2018/00357* (2013.01); *A61B 2018/00577* (2013.01); *A61B 2018/00839* (2013.01); *A61B 2562/0209* (2013.01)

(58) Field of Classification Search
USPC ........................................................ 600/508
See application file for complete search history.

(56) References Cited

U.S. PATENT DOCUMENTS

| | | | |
|---|---|---|---|
| 6,301,496 | B1 | 10/2001 | Reisfeld |
| 7,123,954 | B2 | 10/2006 | Narayan et al. |
| 8,165,666 | B1 | 4/2012 | Briggs et al. |
| 8,224,432 | B2 | 7/2012 | MacAdam et al. |
| 8,275,452 | B2 | 9/2012 | MacAdam et al. |
| 8,306,612 | B2 | 11/2012 | MacAdam |
| 8,340,766 | B2 | 12/2012 | Ryu et al. |
| 8,401,625 | B2 | 3/2013 | Harlev et al. |
| 8,417,313 | B2 | 4/2013 | Scharf et al. |
| 8,433,394 | B2 | 4/2013 | Harlev et al. |
| 8,433,398 | B2 | 4/2013 | Zhang |
| 8,521,266 | B2 | 8/2013 | Narayan et al. |
| 2005/0288599 | A1 | 12/2005 | MacAdam et al. |
| 2007/0232936 | A1 | 10/2007 | Mann et al. |
| 2007/0232949 | A1 | 10/2007 | Saksena |
| 2008/0058794 | A1 | 3/2008 | MacAdam |
| 2008/0281391 | A1 | 11/2008 | MacAdam et al. |
| 2009/0030334 | A1 | 1/2009 | Anderson et al. |
| 2009/0204113 | A1 | 8/2009 | MacAdam et al. |
| 2010/0094274 | A1* | 4/2010 | Narayan ............ A61B 5/046 606/33 |
| 2010/0204585 | A1* | 8/2010 | Zhang ............ A61B 5/0452 600/483 |
| 2011/0251505 | A1 | 10/2011 | Narayan et al. |
| 2012/0283579 | A1 | 11/2012 | Briggs et al. |
| 2013/0066221 | A1 | 3/2013 | Ryu et al. |
| 2013/0150740 | A1 | 6/2013 | Narayan et al. |
| 2013/0150742 | A1 | 6/2013 | Briggs et al. |
| 2015/0073246 | A1 | 3/2015 | Chmiel et al. |

FOREIGN PATENT DOCUMENTS

| | | |
|---|---|---|
| WO | 2011127211 | 10/2011 |
| WO | 2012151008 | 11/2012 |
| WO | 2012151301 | 11/2012 |
| WO | 2013086468 | 6/2013 |
| WO | 2013086469 | 6/2013 |

OTHER PUBLICATIONS

International Search Report and Written Opinion issued in Application No. PCT/US2016/023731, dated Jun. 30, 2016.
International Preliminary Report on Patentability issued in Application No. PCT/US2016/023731, dated Oct. 5, 2017.
Jones et al. "Non-invasice identification of stable rotors and focal sources for human atrial fibrillation:mechanistic classification of atrial fibrillation from the electrocardiogram." Europace, 2013, 15, 1249-1258.
Kawata et al. "Focal Impulse and Rotor Modulation for Paroxysmal Atrial Fibrillation." The Journal of Innovations in Cardiac Rhythm Management, 2013, 4, 1101-1107.
Mazeh et al. "A Simplified Approach for Simultaneous Measurements of Wavefront Velocity and Curvature in the Heart Using Activation Times." Cardiovasc Eng Technol. 2013, 4, 520-534.
Nakagawa et al. "Rapid High Resolution Electroanatomical Mapping: Evaluation of a New System in a Canine Atrial Linear Lesion Model." Circulation Arrythmia and Electrophysiology, 2012, 5, 417-424.
Narayan et al. "Targeting Stable Rotors to Treat Atrial Fibrillation." Arrythmia and Electrophysiology Review, 2012, 1, 34-38.
Narayan et al. "Panoramic Electrophysiological Mapping but not Electrogram Morphology Identifies Stable Sources for Human Atrial Fibrillation: Stable Atrial Fibrillation Rotors and Focal Sources Relate to Fractionated Electrograms." Circulation Arrhythmia and Electrophysiology, 2013, 6, 58-67.
Narayan et al. "Direct or Coincidental Elimination of Stable Rotors or Focal Sources May Explain Successful Atrial Fibrillation Ablation." Journal of the American College of Cardiology, 2013, 6, 138-147.
Pandit et al. "Rotors and the Dynamics of Cardiac Fibrillation." Circulation Research, 2013, 112, 849-862.
Rappel et al. "Theoretical considerations for mapping activation in human cardiac fibrillation." Chaos, 2013, 23, 023113.
Sohn et al. "The Single Equivalent Moving Dipole Model Does not Require Spatial Anatomical Information to Determine Cardiac Sources of Activation." IEEE J Biomed Health Inform. 2014, 18, 222-230.

* cited by examiner

METHODS AND DEVICES FOR SAMPLE CHARACTERIZATION

CROSS-REFERENCE TO RELATED APPLICATIONS

This application is a 371 U.S. National Stage of International Application No. PCT/US2016/023731, filed Mar. 23, 2016, which claims the benefit of priority to U.S. Provisional Application No. 62/136,683, filed Mar. 23, 2015, each of which are hereby incorporated herein by reference in their entireties.

BACKGROUND

Atrial fibrillation is the most common cardiac arrhythmia, eventually affecting over 5% of Americans over age 60, and is associated with high morbidity from recurrent hospitalizations, stroke, and heart failure. The burden is increasing with the aging of the population. The existing treatments include catheter ablation, which is becoming a predominant technique for controlling the arrhythmia. However, unlike for other arrhythmias, the success rate of the ablation procedure for atrial fibrillation is relatively low, with single procedure success rates estimated as low as 50%. One problem is that the disease is not well understood. Because of this, the typical ablation procedure targets a large amount of potential triggering sources for tissue destruction. The decision as to where to ablate is usually not patient-centric.

Recently an approach of identifying sources that may be specific to given individuals as their atrial fibrillation sustaining mechanisms has shown promise in reducing the amount of tissue destruction while improving outcomes. A significant disadvantage, however, is that this technique requires the use of large basket catheters, which are needed to record simultaneously from a large percentage of the surface area of the human left and right atria. These catheters are not typically used for other purposes, and their use predisposes patients to higher risks from the procedure. What are needed are new methods and devices for detecting and/or quantifying atrial fibrillation indicators and other parameters or characteristics. The methods and devices disclosed herein address these and other needs.

SUMMARY

Disclosed herein are methods and devices for the detection, quantification, and/or monitoring of characteristics in samples. The disclosed methods and devices can be used, for example, to identify the presence and location of atrial fibrillation indicators with high spatial resolution. The disclosed methods and devices can even be used to identify the presence and location of atrial fibrillation indicators using non-simultaneously collected data, feats not possible through existing techniques.

Provided herein are methods and systems for determining sample characteristics, such as those relevant for identifying and localizing cardiac arrhythmia indicators. The methods can comprise collecting a first electrical signal collecting a first electrical signal from each of a first plurality of locations in a sample at a first time. The first electrical signals can be processed to obtain a first sample parameter for each of the first plurality of locations in the sample at the first time. The methods can further comprise collecting a second electrical signal from each of a second plurality of locations in a sample at a second time, wherein the first plurality of locations and the second plurality of locations have at least one location in common. The second electrical signals can be processed to obtain a second sample parameter for each of the second plurality of locations in the sample at the second time. The second sample parameters can be compared to the first sample parameters to obtain a third sample parameter at each of the first plurality of locations and the second plurality of locations. The third sample parameters can be processed to determine a sample characteristic.

The first electrical signal can, for example, comprise voltage. In some implementations, processing the first electrical signals comprises applying a transform function, a trigonometric function, or a combination thereof. In some examples, the first sample parameter comprises frequencies, phases or a combination thereof at each of the first plurality of locations.

The second electrical signal can, for example, comprise voltage. In some implementations, processing the second electrical signals comprises applying a transform function, a trigonometric function, or a combination thereof. In some implementations, processing the second electrical signals comprises applying a Fourier transform and an arctangent function. In some examples, the second sample parameter comprises frequencies, phases or a combination thereof at each of the second plurality of locations.

In some implementations, comparing the second sample parameters and the first sample parameters comprises applying a correction function to the second sample parameters to obtain the third sample parameters. For example, the correction function can be determined based on a phase difference between the first sample parameter and the second sample parameter at the location in common between the first plurality of locations and the second plurality of locations.

The third sample parameter can comprise frequencies and phases at each of the first plurality of locations and the second plurality of locations. Processing the third sample parameters can, in some implementations, comprise mesh generation from the third sample parameters to obtain a sample characteristic. In some examples, the mesh generation comprises triangulating or tetrahedralizing the third sample parameters. In some implementations, the processing of the third sample parameters results in the generation of a sample characteristic, which can, for example, be a two or three-dimensional spatially-sampled phase map of a periodic cardiac arrhythmia sustainer mechanism.

In some examples, the third sample parameter can be used as a new first sample parameter, and a new set of electrical signals can be collected and/or processed to comprise a new second sample parameter. In some examples, the new first sample parameter and the new second parameter can be compared to obtain a new third sample parameter. Thus, in some examples, the method can be carried out iteratively.

Also disclosed herein are methods for identifying a cardiac arrhythmia indicator in a subject. In some implementations, the methods can comprise inserting a catheter into a heart cavity, wherein the catheter comprises a plurality of electrodes. The electrodes can be positioned at a first plurality of locations and a first electrical signal can be collected from each of the electrodes at a first time. The method can further comprise positioning the electrodes at a second plurality of locations, wherein the first plurality of locations and the second plurality of locations have at least one location in common. A second electrical signal can be collected from each of the electrodes at a second time. The method can further comprise processing the first electrical signals at the first time to obtain a first phase function for each of the first plurality of locations and processing the second electrical signals at the second time to obtain a second phase function for each of the second plurality of locations. The second phase functions can be corrected based on the first phase functions to obtain a third phase function at each of the first plurality of locations and second plurality of locations. The method can further comprise processing the third phase functions to obtain a cardiac arrhythmia indicator.

In some implementations, the method further comprises selecting a course of therapy for the subject based on the cardiac arrhythmia indicator. Selecting a course of therapy for the subject can, for example, comprise selective ablation of cardiac tissue at the locations in the heart cavity containing the cardiac arrhythmia indicator.

The methods disclosed herein can be carried out in whole or in part on one or more computing devices.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
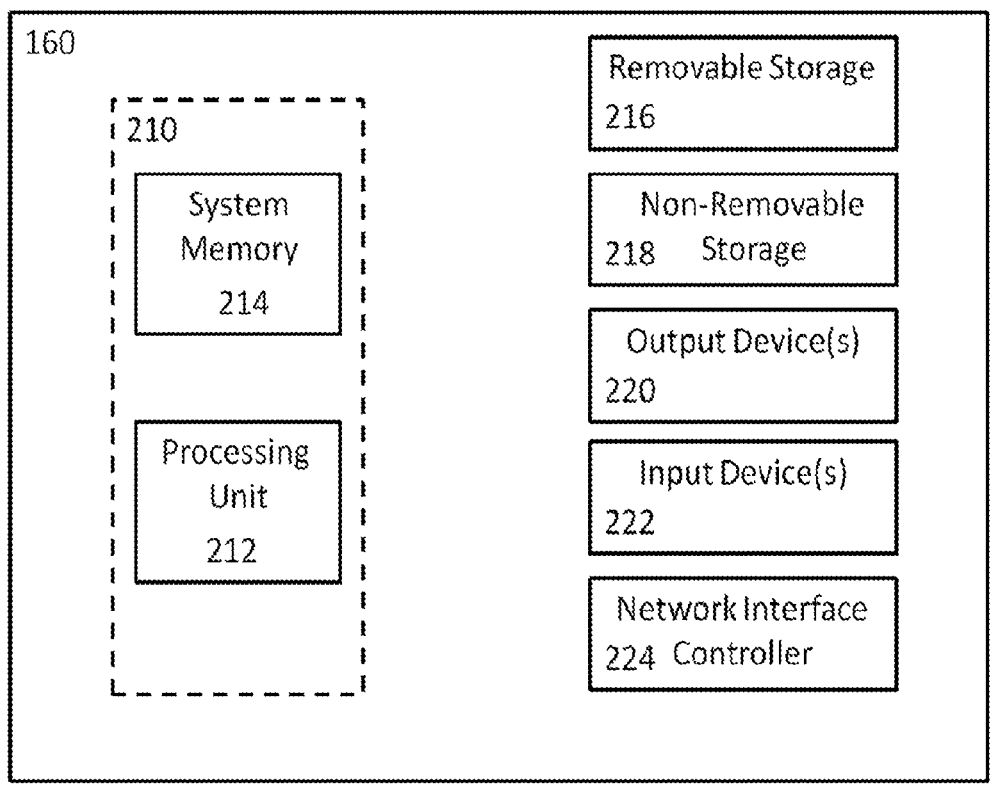
FIG. 1 is a schematic of an exemplary computing device.

The methods and devices described herein may be understood more readily by reference to the following detailed description of specific aspects of the disclosed subject matter, figures and the examples included therein.

Before the present methods and devices are disclosed and described, it is to be understood that the aspects described below are not intended to be limited in scope by the specific systems, methods, articles, and devices described herein, which are intended as illustrations. Various modifications of the systems, methods, articles, and devices in addition to those shown and described herein are intended to fall within the scope of that described herein. Further, while only certain representative systems and method steps disclosed herein are specifically described, other combinations of the systems and method steps also are intended to fall within the scope of that described herein, even if not specifically recited. Thus, a combination of steps, elements, components, or constituents may be explicitly mentioned herein or less, however, other combinations of steps, elements, components, and constituents are included, even though not explicitly stated.

Reference will now be made in detail to specific aspects of the disclosed methods and devices, examples of which are illustrated in the accompanying examples and figures.

Provided herein are methods and systems for determining sample characteristics, such as cardiac arrhythmia indicators. The methods can comprise collecting a first electrical signal from each of a first plurality of locations in a sample at a first time. The first electrical signals can be processed to obtain a first sample parameter for each of the first plurality of locations in the sample at the first time. The methods can further comprise collecting a second electrical signal from each of a second plurality of locations in a sample at a second time, wherein the first plurality of locations and the second plurality of locations have at least one location in common. The second electrical signals can be processed to obtain a second sample parameter for each of the second plurality of locations in the sample at the second time. The second sample parameters can be compared to the first sample parameters to obtain a third sample parameter at each of the first plurality of locations and the second plurality of locations. The third sample parameters can be processed to determine a sample characteristic.

It is understood that throughout this specification the identifiers "first", "second" and "third" are used solely to aid in distinguishing the various components and steps of the disclosed subject matter. The identifiers "first", "second" and "third" are not intended to imply any particular order, amount, preference, or importance to the components or steps modified by these terms.

In some implementations, the sample comprises an organ. The organ can be any organ from which electrical signals can be collected, such as, for example, a heart or a brain. In some examples, the sample comprises a heart.

The first electrical signal can, for example, comprise voltage (e.g., unipolar voltage, bipolar voltage), frequency, phase, vector conduction velocity, or a combination thereof. In some implementations, the first electrical signal comprises voltage. In some implementations, the first electrical signal comprises unipolar voltage as a function of time.

In some implementations, processing the first electrical signals comprises applying a transform function, a trigonometric function, or a combination thereof. Examples of transform functions include, but are not limited to Fourier transforms, wavelet transforms, Hilbert transforms, and combinations thereof. Examples of trigonometric functions include, but are not limited to, a tangent function, cotangent function, arctangent function, and combinations thereof. In some implementations, processing the first electrical signals comprises applying a Fourier transform and an arctangent function. A Fourier transform can, for example, be used to transform a signal between the time or spatial domains and the frequency domain. In some examples, the arctangent of the real and imaginary components for a frequency from a Fourier transform calculation can be used to calculate the phase at that frequency. The phase, as an angle, can range between 0 and 360 degrees.

In some examples, the first sample parameter comprises frequencies, phases or a combination thereof at each of the first plurality of locations.

The second electrical signal can, for example, comprise voltage. In some implementations, processing the second electrical signals comprises applying a transform function, a trigonometric function, or a combination thereof. In some implementations, processing the second electrical signals comprises applying a Fourier transform and an arctangent function. In some examples, the second sample parameter comprises frequencies, phases or a combination thereof at each of the second plurality of locations.

In some implementations, comparing the second sample parameters and the first sample parameters comprises applying a correction function to the second sample parameters to obtain the third sample parameters. For example, the correction function can be determined based on a phase difference between the first sample parameter and the second sample parameter at the location in common between the first plurality of locations and the second plurality of locations.

The third sample parameter can comprise frequencies and phases at each of the first plurality of locations and the second plurality of locations. The first plurality of locations and the second plurality of locations have at least one location in common, therefore the electrical signal from the same location was collected twice, once at the first time (e.g., in the first electrical signals) and once at the second time (e.g., in the second electrical signals). The phase (for a given frequency of interest) at that location can be assumed to be constant, as long as the arrhythmia maintaining mechanism generating that frequency is constant, so the difference in the phase measurements at that location can be applied to the phase measurements (e.g., the second sample parameters) from each of the second plurality of locations at the second time, bringing their phase measurements (e.g., the second sample parameters) into alignment with those of the first sample parameters.

Processing the third sample parameters can, for example, comprise mesh generation of the third sample parameters to obtain a sample characteristic. In some examples, the mesh generation comprises triangulating or tetrahedralizing the third sample parameters. For example, the third sample parameters can comprise an estimate of the phase at each of the locations (in x,y,z coordinates). This data can then be treated as a point cloud where each point has an (x,y,z) coordinate and a phase value. This point cloud can then be tetrahedralized (3D) or triangulated (2D), creating an array of triangles or tetrahedrons consisting of points from the point cloud such that no point is inside of a triangle/tetrahedron. This can be accomplished using established techniques. A graphic visualization of the result can be produced by interpolating the phase on a visible surface of a triangle or tetrahedron from the phase of the vertex points. The result is a solid shape representing the recorded 3D surface of the chamber of the heart that was mapped, with a value for the estimated phase at each location, despite not having recorded from each of these locations simultaneously.

In some implementations, the method further comprises collecting one or more additional electrical signals from one or more additional plurality of locations, wherein the one or more additional plurality of locations have at least one location in common with the first plurality of locations, the second plurality of locations, or a combination thereof. The one or more additional electrical signals from the one or more additional plurality of locations can, for example, be processed according to the methods described above for the first electrical signals and second electrical signals.

The sample characteristic can, for example, comprise a cardiac arrhythmia indicator. Cardiac arrhythmia indicators include, but are not limited to, rotors, focal impulses and combinations thereof. If more than one is present in a subject, they are assumed to have different periodicities (i.e., frequencies). The dominant frequencies can be determined using standard techniques and each of these can be investigated according to any of the methods described herein. For example, the graphic visualization of the tetrahedralized or triangularized point cloud representing the recorded 3D surface of the chamber of the heart that was mapped, with a value for the estimated phase at each location. This representation can be generated for each of the dominant frequencies identified; each of these representations can be a sample characteristic. This representation can then be used to identify rotors, which are spiral reentrant phenomena identified by the presence of all possible phases between 0 and 360 degrees within a constrained area, and focal impulses, which are locations with an arbitrary phase surrounded in all directions within a constrained area by locations with all higher or lower phases.

Also disclosed herein are methods for obtaining a cardiac arrhythmia indicator in a subject. The term "subject" refers to any individual who is the target of administration or treatment. The subject can be a vertebrate, for example, a mammal. Thus, the subject can be a human or veterinary patient.

In some implementations, the methods can comprise inserting a catheter into a heart cavity, wherein the catheter comprises a plurality of electrodes. The catheter can be any type of catheter suitable for use in a heart cavity. The electrodes can be positioned at a first plurality of locations and a first electrical signal can be collected from each of the electrodes at a first time. The method can further comprise positioning the electrodes at a second plurality of locations, wherein the first plurality of locations and the second plurality of locations have at least one location in common. A second electrical signal can be collected from each of the electrodes at a second time. The method can further comprise processing the first electrical signals at the first time to obtain a first phase function for each of the first plurality of locations and processing the second electrical signals at the second time to obtain a second phase function for each of the second plurality of locations. The second phase functions can be corrected based on the first phase functions to obtain a third phase function at each of the first plurality of locations and second plurality of locations. The method can further comprise processing the third phase functions to obtain a cardiac arrhythmia indicator.

In some examples, the method can further comprise positioning the electrodes at one or more additional plurality of locations, wherein the one or more additional plurality of locations have at least one location in common with the first plurality of locations, the second plurality of locations, or a combination thereof, and collecting one or more additional electrical signals from the electrodes at each of the one or more additional plurality of locations. The one or more additional electrical signals from the one or more additional plurality of locations can, for example, be processed according to the methods of described above.

In some examples, the method can comprise inserting a plurality of catheters into a heart cavity, wherein each catheter comprises one or more electrodes. The electrodes can be positioned at a first plurality of locations and a first electrical signal can be collected from each of the electrodes at a first time. The method can further comprise positioning the electrodes at a second plurality of locations, wherein the first plurality of locations and the second plurality of locations have at least one location in common. In some examples, one catheter can remain in the same location while the other catheters are moved. In some examples, all the catheters can be moved to new locations. A second electrical signal can be collected from each of the electrodes at a second time. The method can further comprise processing the first electrical signals at the first time to obtain a first phase function for each of the first plurality of locations and processing the second electrical signals at the second time to obtain a second phase function for each of the second plurality of locations. The second phase functions can be corrected based on the first phase functions to obtain a third phase function at each of the first plurality of locations and second plurality of locations. The method can further comprise processing the third phase functions to obtain a cardiac arrhythmia indicator.

In some examples, the method can further comprise positioning the electrodes at a one or more additional plurality of locations, wherein the one or more additional plurality of locations have at least one location in common with the first plurality of locations, the second plurality of locations, or a combination thereof. The method can further comprise collecting an electrical signal from each of the electrodes at the one or more additional plurality of locations at one or more additional times. The one or more additional electrical signals from the one or more additional plurality of locations can, for example, be processed according to the methods described above for the first electrical signals and second electrical signals to obtain a phase function for each of the one or more additional plurality of locations. The method can further comprise, for example, correcting the phase functions based on the accumulated phase functions to obtain a new accumulated phase function at each of the one or more accumulated additional plurality of locations. The accumulated phased function can, in some implementations, be processed to obtain a cardiac arrhythmia indicator.

In some implementations, the method further comprises selecting a course of therapy for the subject based on the cardiac arrhythmia indicator. The term "therapy" refers to the medical management of a subject with the intent to cure, ameliorate, stabilize, or prevent a disease, pathological condition, or disorder. This term includes active therapy, that is, therapy directed specifically toward the improvement of a disease, pathological condition, or disorder, and also includes causal therapy, that is, therapy directed toward removal of the cause of the associated disease, pathological condition, or disorder. In addition, this term includes palliative therapy, that is, therapy designed for the relief of symptoms rather than the curing of the disease, pathological condition, or disorder; preventative therapy, that is, therapy directed to minimizing or partially or completely inhibiting the development of the associated disease, pathological condition, or disorder; and supportive therapy, that is, therapy employed to supplement another specific therapy directed toward the improvement of the associated disease, pathological condition, or disorder.

Selecting a course of therapy for the subject can, for example, comprise selective ablation of cardiac tissue at the locations in the heart cavity containing the cardiac arrhythmia indicator.

The methods disclosed herein can be carried out in whole or in part on one or more computing devices.

Figure 2:
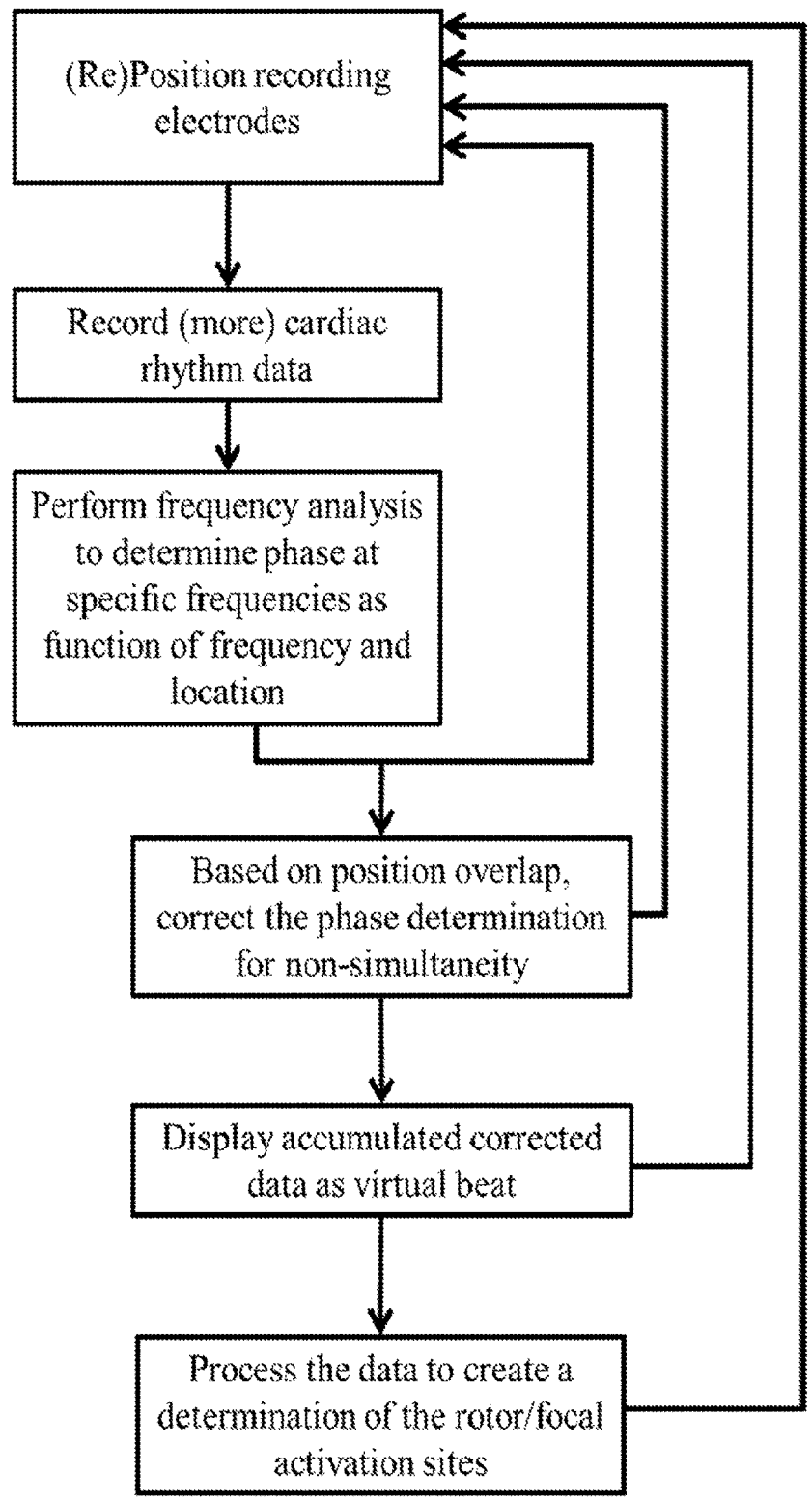
FIG. 2 is a summary of the methods discussed herein.

Also disclosed herein are computing devices to receive and process the electrical signals from the sample, as discussed in more detail below. FIG. 1 illustrates an example computing device upon which examples disclosed herein may be implemented. The computing device (160) can include a bus or other communication mechanism for communicating information among various components of the computing device (160). In its most basic configuration, computing device (160) typically includes at least one processing unit (212) (a processor) and system memory (214). Depending on the exact configuration and type of computing device, system memory (214) may be volatile (such as random access memory (RAM)), non-volatile (such as read-only memory (ROM), flash memory, etc.), or some combination of the two. This most basic configuration is illustrated in FIG. 2 by a dashed line (210). The processing unit (212) may be a standard programmable processor that performs arithmetic and logic operations necessary for operation of the computing device (160).

The computing device (160) can have additional features/functionality. For example, computing device (160) may include additional storage such as removable storage (216) and non-removable storage (218) including, but not limited to, magnetic or optical disks or tapes. The computing device (160) can also contain network connection(s) (224) that allow the device to communicate with other devices. The computing device (160) can also have input device(s) (222) such as a keyboard, mouse, touch screen, antenna or other systems configured to communicate with the camera in the system described above, etc. Output device(s) (220) such as a display, speakers, printer, etc. may also be included. The additional devices can be connected to the bus in order to facilitate communication of data among the components of the computing device (160).

The processing unit (212) can be configured to execute program code encoded in tangible, computer-readable media. Computer-readable media refers to any media that is capable of providing data that causes the computing device (160) (i.e., a machine) to operate in a particular fashion. Various computer-readable media can be utilized to provide instructions to the processing unit (212) for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit (212) can execute program code stored in the system memory (214). For example, the bus can carry data to the system memory (214), from which the processing unit (212) receives and executes instructions. The data received by the system memory (214) can optionally be stored on the removable storage (216) or the non-removable storage (218) before or after execution by the processing unit (212).

The computing device (160) typically includes a variety of computer-readable media. Computer-readable media can be any available media that can be accessed by device (160) and includes both volatile and non-volatile media, removable and non-removable media. Computer storage media include volatile and non-volatile, and removable and non-removable media implemented in any method or technology for storage of information such as computer readable instructions, data structures, program modules or other data. System memory (214), removable storage (216), and non-removable storage (218) are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device (160). Any such computer storage media can be part of computing device (160).

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, system memory (214) comprises computer-executable instructions stored thereon that, when executed by the processor (212), provide for analysis of signals captured from the sample to obtain information about the sample (i.e., one or more sample characteristics, such as cardiac arrhythmia indicators). To implement analysis of this type, system memory (214) can comprise computer-executable instructions stored thereon that, when executed by the processor (212), cause the processor to: receive a first electrical signal from each of a first plurality of locations in a sample at a first time; process the first electrical signals to obtain a first sample parameter for each of the first plurality of locations in the sample at the first time; receive a second electrical signal from each of a second plurality of locations in a sample at a second time, wherein the first plurality of locations and the second plurality of locations have at least one location in common; process the second electrical signals to obtain a second sample parameter for each of the second plurality of locations in the sample at the second time; compare the second sample parameters to the first sample parameters to obtain a third sample parameter at each of the first plurality of locations and the second plurality of locations; and process the third sample parameters to determine a sample characteristic.

In some implementations, the sample comprises a heart. In certain examples, catheters (manipulatable and deflectable/deformable cables with a shaped tip with 2 or more bare metal recording surfaces (electrodes)) can be introduced into the heart chamber of interest (typically the left or right atrium). Commercially available mapping systems exist, any of which can be used, that use a variety of techniques to determine the 3D position, in Cartesian coordinates, of each of the metal electrodes on each catheter within the heart, as function of time, while also recording the small electrical signals produced by the heart tissue close to the electrode. Signals can be recorded by comparing the voltage on an electrode with another voltage, possibly that recorded at a nearby electrode (bipolar signal), or less nearby electrode (unipolar signal). The mapping systems record the electrical signal by sampling the voltage on the electrode many times a second, producing a sampled, not continuous waveform. A given catheter, for example, a lasso shaped catheter (hereafter referred to as a Lasso), with its 20 electrodes, will be kept in a position in the heart by the operator until an adequate signal is recorded, then moved to another location and the process repeated as needed.

The catheter data, e.g. from a Lasso catheter, can take the form of the location signal, which carries the location in (x,y,z) coordinates sampled an arbitrary number of times per second, as well as the voltage recording, which is also sampled an arbitrary number of times per second. Each of these signals is obtained simultaneously or near-simultaneously for each electrode of the catheter.

The location signal can first be used to verify the stability of the catheter in space during the voltage recording. Using a clustering algorithm, subsets (or segments) of the total recording time during which the catheter remains at a stable location can be identified, and the times during which the catheter was moving can then be excluded. If the duration of time meets certain quality criteria, it is kept. A "segment" from now on refers to the duration of time during which voltage recordings from 'N' electrodes which remained stable in a specific location, is available. From a subject, an arbitrary number of these segments can be obtained, each of which contains the data for simultaneously recorded signals from many electrodes at different locations in space. From one segment to another, the recordings are not simultaneous, but within a segment, they are.

From these segments, the dominant frequency of interest can be identified. This can be done by taking all the available voltage recordings from the chamber(s) of interest, and calculating the power spectrum (using any of a variety of well established techniques, e.g. by applying a Fourier transform) on them. The clinically relevant dominant frequencies in human atrial fibrillation lie between 2 and 19 Hz. The phase at the dominant frequency (or frequencies) can then be identified by taking the arc tangent of the imaginary and real components for the frequency of interest from the Fourier Transform calculation. The phase, as an angle, ranges between 0 and 360 degrees.

Next, the phases are corrected for non-simultaneity. For example, any segment for which no electrode location overlaps with an electrode location from any other segment can be identified and eliminated from the data to be processed. All remaining segments can then be sorted through iteratively to find any segments that overlap. When a match is found, all the phases in that segment can then be corrected. By definition, an overlapping segment means that the signal from the same location was sampled twice, once in each segment. The phase at that location can be assumed to be constant, so the difference in the phase measurements at that location can be applied to the phase measurements from all the electrodes at the second segment, bringing their phase measurements into alignment with those of the first segment.

Thus, an estimate of the phase at each of the locations (in x,y,z coordinates) for which an electrode in a segment can be acquired. This data can then be treated as a point cloud where each point has an (x,y,z) coordinate and a phase value. This point cloud can then be tetrahedralized (3D) or triangulated (2D) using established techniques, creating an array of triangles or tetrahedrons consisting of points from the point cloud such that no point is inside of a triangle/ tetrahedron. A graphic visualization of the result can then be produced. The result is a solid shape representing the recorded 3D surface of the chamber of the heart that was mapped, with a value for the estimated phase at each location, despite not having recorded from each of these locations simultaneously.

This representation can then be used to identify 'rotors', a spiral reentrant phenomena identified by the presence of all possible phases between 0 and 360 degrees within a constrained area, and 'focal impulses', defined as a point with an arbitrary phase surrounded in all directions within a constrained area by points with all higher or lower phases. These areas can be displayed to the user as potential targets for ablative therapy on a 3D representation of the heart chamber of interest.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

Atrial fibrillation is the most common cardiac arrhythmia, eventually affecting over 5% of Americans over age 60, and is associated with high morbidity from recurrent hospitalizations, stroke, and heart failure. The burden is increasing with the aging of the population. The existing treatments include catheter ablation, which is becoming a predominant technique for controlling the arrhythmia. However, unlike for other arrhythmias, the success rate of the ablation procedure for atrial fibrillation is relatively low, with single procedure success rates estimated as low as 50%. One problem is that the disease is not well understood. Because of this, the typical ablation procedure targets for tissue destruction a large amount of potential triggering sources. The decision as to where to ablate is usually not patient-centric.

The established techniques typically target pulmonary vein and other "triggers" for atrial fibrillation. This is done by creating lines of conduction block within the left atrial endocardial surface using heat and other energy sources. The end result is to prevent triggering depolarizations from leaving their sites of origin and affecting the rest of the heart.

Recently an approach of identifying, using frequency-domain analysis, the "rotors" and "focal impulse" sources that may be specific to given individuals as their atrial fibrillation maintaining mechanisms, has shown promise in reducing the amount of tissue destruction while improving outcomes. This system is being produced and developed by Topera™. A significant disadvantage however, is that this technique requires the use of large basket catheters, which are needed to simultaneously record from a large percentage of the surface area of the human left and right atria simultaneously. These catheters are not typically used for other purposes, and their use predisposes patients to higher risks from the procedure. The methods discussed herein address this problem in that the methods can use the same types of movable catheters that are widely used for many procedures, and which are comfortably employed by many electrophysiologists around the world. Rather, by performing frequency domain analysis using this algorithm, one could incrementally and quickly build a picture for a given patient at potentially much higher spatial resolution, of their atrial fibrillation sustaining mechanisms (rotors/focal impulses), and these could be targeted for ablation instead of or in addition to the current targets. This approach could leverage the use of existing technology, equipment, and experience.

Some of the advantages of the methods discussed herein are: 1) existing and widely used multi-electrode catheters, which many electrophysiologists feel comfortable with, can be used; 2) with these, a much higher spatial resolution phase-map of the atria can be created (whereas the basket catheter used for simultaneously recording from many (64) sites in the heart is spaced with electrodes at least a centimeter apart, and not all of them will be making contact with the heart); 3) the method can be incremental, as a dominant frequency is identified, partial mapping can point towards the rotors, allowing for more efficient workflow during procedures; (4) the methods could be implemented on top of existing mapping systems which are already widely used and distributed. A software upgrade with minimal hardware changes could potentially facilitate widespread distribution of the ability to target rotors, without requiring major capital purchases to purchase a Topera™ system for example, in addition to a mapping system.

The methods discussed herein can transform input data into an output representation that can be used to identify areas in the heart that can be targets for catheter ablation for treatment of arrhythmias. The arrhythmia that could be treated with this technique can be any arrhythmia, such as, for example, atrial fibrillation. 'Rotors' and 'focal impulses' are dynamic phenomena that are felt to be somewhat stable in location in a given patient, but differ in location from one patient to another. A typical patient may have one to a few of these. A rotor represents a spiral wave, much like the arms of a hurricane, and these are phenomena seen throughout nature and in biology, in cardiac and possibly in neural tissue under certain pathological conditions. In cardiac tissue, the problem of identifying a spiral wave occurs due to imperfect and incomplete information regarding the state of the tissue, and due to the difficulty of interpreting repetitive and noisy activations in the time domain to identify a periodic phenomenon.

The input data for the method is obtained during an electrophysiologic study, which is a non-surgical procedure. During this procedure, catheters (manipulatable and deflectable/deformable cables with a shaped tip with up to 20 or more bare metal recording surfaces (electrodes)) are introduced into the heart chamber of interest (typically the left or right atrium). Commercially available mapping exist, any of which can be used, that use a variety of techniques to determine the 3D position, in Cartesian coordinates, of each of the metal electrodes on each catheter within the heart, as function of time, while also recording the small electrical signals produced by the heart tissue close to the electrode. Signals are recorded by comparing the voltage on an electrode with another voltage, possibly that recorded at a nearby electrode (bipolar signal), or less nearby electrode (unipolar signal). The signals produced by the tissue are continuous waveforms influenced by the depolarization and repolarization of nearby cardiomyocytes. In addition, there may be a component of contaminating signals from more distant electrical signal sources, such as from other (further) areas of the heart, other muscles in the body, and electrical noise from the room in which the procedure is performed. The mapping systems record the electrical signal by sampling the voltage on the electrode many times a second, producing a sampled, not continuous waveform. A given catheter, for example, a lasso shaped catheter (hereafter referred to as a Lasso), with its 20 electrodes, will be kept in a position in the heart by the operator until an adequate signal is recorded, then moved to another location and the process repeated as needed.

The catheter data, e.g. from a Lasso catheter, will be taken from the mapping system, or directly from the catheter using custom hardware to replace the mapping system. This data can take the form of the location signal, which carries the location in (x,y,z) coordinates sampled an arbitrary number of times per second, as well as the voltage recording, which is also sampled an arbitrary number of times per second. Each of these signals is obtained simultaneously or near-simultaneously for each electrode of the catheter. It can take at least 1-2 seconds, but preferably longer, to collect tracings at each location.

The location signal can first be used to verify the stability of the catheter in space during the voltage recording. Using a clustering algorithm, subsets (or segments) of the total recording time during which the catheter remains at a stable location can be identified, and the times during which the catheter was moving can then be excluded. If the duration of time meets certain quality criteria, it is kept. A "segment" from now on refers to the duration of time during which voltage recordings from 'N' electrodes (typically 20) which remained stable in a specific location, is available.

From a patient, an arbitrary number of these segments can be obtained, each of which contains the data for simultaneously recorded signals from many electrodes at different locations in space. From one segment to another, the recordings are not simultaneous, but within a segment, they are.

From these segments, the dominant frequency of interest can be identified. This can be done by taking all the available voltage recordings from the chamber(s) of interest, and calculating the power spectrum (using any of a variety of well established techniques) on them. The clinically relevant dominant frequencies in human atrial fibrillation lie between 2 and 19 Hz.

For example, all the voltage signals can be subsampled to 100 Hz to facilitate further analysis. A Fourier transform can then be applied to calculate the power spectrum in dB. The power spectrum can then be used to identify peaks at the frequency or frequencies between 2 and 19 Hz. The strength of the dominant frequency (or frequencies) can be represented as the ratio of the power (in dB) to the average power (in dB) for all the frequency bins between 2 and 19 Hz. The phase at the dominant frequency (or frequencies) can then be identified by taking the arc tangent of the imaginary and real components for the frequency of interest from the Fourier Transform calculation. The phase, as an angle, ranges between 0 and 360 degrees.

Next, the phases are correct for non-simultaneity. For a given frequency of interest, the phase at a point is comparable from one electrode to another from the same segment, but not to a recording from an electrode in another segment. These phases are not aligned to each other. However, if an electrode location in one segment (#2) overlaps with the location of an electrode in another segment (#1), then the signals from that electrode can be used to correct (align) the phases of all the electrodes in segment #2 so they are consistent and can be compared with those from segment #1.

For example, any segment for which no electrode location overlaps with an electrode location from any other segment can be identified. Overlap is defined as being within a certain Cartesian distance. The cutoff selected is a user-selectable parameter that influences the time quality trade-off of the end-result. These segments are placed in a 'black' list, marked such so they will not be further processed. All remaining segments are then marked as being in the 'red' list. These segments can then be sorted by the average power across electrodes at the selected frequency bin, such that segments with higher mean power at that frequency are listed first. Staring at the beginning of this list, one of these segments (a 'seed') can be selected and moved from the 'red' list to the 'green' list. The 'red' list can then be sorted through iteratively to find any segments that overlap with a segment in the 'green' list. When a match is found, all the phases in that segment can then be corrected. By definition, an overlapping segment means that the signal from the same location was sampled twice, once in each segment. The phase at that location can be assumed to be constant, so the difference in the phase measurements at that location can be applied to the phase measurements from all the electrodes at the second segment, bringing their phase measurements into alignment with those of the first segment. This segment is now moved into the 'green' list. When no additional 'red' list segments can be moved over to the 'green' list, iteration can be stopped. If more than half of all segments have not been accumulated into the 'green' list, then the initial 'seed' was not a good 'seed' and the process can be repeated, picking a different element from the 'red' list to be the 'seed'.

Thus, an estimate of the phase at each of the locations (in x,y,z coordinates) for which an electrode in a segment is available in the 'green' list can be acquired. This data can then be treated as a point cloud where each point has an (x,y,z) coordinate and a phase value. This point cloud can then be tetrahedralized (3D) or triangulated (2D), creating an array of triangles or tetrahedrons consisting of points from the point cloud such that no point is inside of a triangle/tetrahedron. This can be accomplished using established techniques. A graphic visualization of the result can be produced by interpolating the phase on a visible surface of a triangle or tetrahedron from the phase of the vertex points. The result is a solid shape representing the recorded 3D surface of the chamber of the heart that was mapped, with a value for the estimated phase at each location, despite not having recorded from each of these locations simultaneously.

This representation can then be used to identify 'rotors', a spiral reentrant phenomena identified by the presence of all possible phases between 0 and 360 degrees within a constrained area, and 'focal impulses', defined as a point with an arbitrary phase surrounded in all directions within a constrained area by points with all higher or lower phases. These areas can be displayed to the user as potential targets for ablative therapy on a 3D representation of the heart chamber of interest.

FIG. 2 displays an outline of the methods discussed herein, which have been elucidated more fully above. It should be readily apparent that the methods presented herein present many options for dynamic feedback in the process, where at any point in the method the electrodes can be repositioned and more data can be collected to build up an ever larger data set to help further increase the resolution of data acquired within the heart. The methods discussed herein allow for the phases to be continually corrected as more data is acquired, essentially allowing several smaller phase maps to be continually "stitched together" into a larger, higher resolution phase map. One of the benefits of adding more and more data points is that more and different dominant frequencies can be identified, ultimately allowing for the identification of larger numbers of arrhythmia sustaining mechanisms such as rotors and/or focal sources.

The methods presented herein occur in the frequency and phase domains and discuss mechanisms by which data can be collected at a variety of time points, i.e. not all simultaneously, and then corrected for the non-simultaneity.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible examples may be made of the invention without departing from the scope thereof, it is to be understood that all matter herein set forth or shown in the accompanying drawings is to be interpreted as illustrative and not in a limiting sense.

What is claimed is:

1. A method, comprising:
   collecting a first electrical signal from each of a first plurality of locations in a sample at a first time;
   processing the first electrical signals to obtain a first sample parameter for each of the first plurality of locations in the sample at the first time;
   collecting a second electrical signal from each of a second plurality of locations in a sample at a second time;
   wherein the first plurality of locations and the second plurality of locations have at least one location in common;
   processing the second electrical signals to obtain a second sample parameter for each of the second plurality of locations in the sample at the second time;
   comparing the second sample parameters to the first sample parameters to obtain a third sample parameter at each of the first plurality of locations and the second plurality of locations,
      wherein comparing the second sample parameters and the first sample parameters comprises applying a correction function to the second sample parameters to obtain the third sample parameters,
      wherein the correction function is determined based on a phase difference between the first sample parameter and the second sample parameter at the location in common between the first plurality of location and the second plurality of locations; and
   processing the third sample parameters to determine a sample characteristic.

2. The method of claim 1, wherein the sample comprises an organ.

3. The method of claim 1, wherein the organ comprises the heart.

4. The method of claim 1, wherein the first electrical signal, the second electrical signal, or a combination thereof comprises voltage.

5. The method of claim 1, wherein processing the first electrical signals, the second electrical signals, or a combination thereof comprises applying a transform function, a trigonometric function, or a combination thereof.

6. The method of claim 1, wherein processing the first electrical signals, the second electrical signals, or a combination thereof comprises applying a Fourier transform and an arctangent function.

7. The method of claim 1, wherein the first sample parameter comprises frequencies, phases or a combination thereof at each of the first plurality of locations; the second sample parameter comprises frequencies, phases, or a combination thereof at each of the second plurality of locations; the third sample parameter comprises frequencies and phases at each of the first plurality of locations and the second plurality of locations; or a combination thereof.

8. The method of claim 1, wherein processing the third sample parameters comprises mesh generation of the third sample parameters to obtain a sample characteristic.

9. The method of claim 8, wherein the mesh generation comprises triangulating or tetrahedralizing the third sample parameters.

10. The method of claim 1, wherein the sample characteristic comprises a cardiac arrhythmia indicator.

11. The method of claim 1, wherein the sample characteristic comprises a rotor or a focal impulse.

12. A method for obtaining a cardiac arrhythmia indicator in a subject, comprising
   inserting a catheter into a heart cavity, wherein the catheter comprises a plurality of electrodes;
   positioning the electrodes at a first plurality of locations;
   collecting a first electrical signal from each of the electrodes at a first time;
   positioning the electrodes at a second plurality of locations; wherein the first plurality of locations and the second plurality of locations have at least one location in common;
   collecting a second electrical signal from each of the electrodes at a second time;
   processing the first electrical signals at the first time to obtain a first phase function for each of the first plurality of locations;
   processing the second electrical signals at the second time to obtain a second phase function for each of the second plurality of locations;
   correcting the second phase functions based on the first phase functions to obtain a third phase function at each of the first plurality of locations and second plurality of locations; and
   processing the third phase functions to obtain a cardiac arrhythmia indicator,
   wherein processing the first electrical signals, the second electrical signals, or a combination thereof comprises applying a Fourier transform and an arctangent function.

13. The method of claim 12, wherein the first electrical signal, the second electrical signal, or a combination thereof comprises voltage.

14. The method of claim 12, wherein processing the third phase functions comprises triangulating or tetrahedralizing the third sample parameters.

15. The method of claim 12, wherein the cardiac arrhythmia indicator comprises a rotor or a focal impulse.

16. The method of claim 12, further comprising selecting a course of therapy for the subject based on the cardiac arrhythmia indicator.

17. The method of claim 16, wherein selecting a course of therapy for the subject comprises selective ablation of cardiac tissue at the locations in the heart cavity containing the cardiac arrhythmia indicator.

18. A method, comprising:
   collecting a first electrical signal from each of a first plurality of locations in a sample at a first time;
   processing the first electrical signals to obtain a first sample parameter for each of the first plurality of locations in the sample at the first time;
   collecting a second electrical signal from each of a second plurality of locations in a sample at a second time;
   wherein the first plurality of locations and the second plurality of locations have at least one location in common;

processing the second electrical signals to obtain a second sample parameter for each of the second plurality of locations in the sample at the second time;

comparing the second sample parameters to the first sample parameters to obtain a third sample parameter at each of the first plurality of locations and the second plurality of locations; and processing the third sample parameters to determine a sample characteristic, wherein processing the first electrical signals, the second electrical signals, or a combination thereof comprises applying a Fourier transform and an arctangent function.

19. The method of claim 18, wherein the sample comprises an organ.

20. The method of claim 18, wherein the organ comprises the heart.

21. The method of claim 18, wherein the first electrical signal, the second electrical signal, or a combination thereof comprises voltage.

22. The method of claim 18, wherein processing the first electrical signals, the second electrical signals, or a combination thereof comprises applying a transform function, a trigonometric function, or a combination thereof.

23. The method of claim 18, wherein the first sample parameter comprises frequencies, phases or a combination thereof at each of the first plurality of locations; the second sample parameter comprises frequencies, phases, or a combination thereof at each of the second plurality of locations; the third sample parameter comprises frequencies and phases at each of the first plurality of locations and the second plurality of locations; or a combination thereof.

24. The method of claim 18, wherein comparing the second sample parameters and the first sample parameters comprises applying a correction function to the second sample parameters to obtain the third sample parameters, wherein the correction function is determined based on a phase difference between the first sample parameter and the second sample parameter at the location in common between the first plurality of location and the second plurality of locations.

25. The method of claim 18, wherein processing the third sample parameters comprises mesh generation of the third sample parameters to obtain a sample characteristic.

26. The method of claim 25, wherein the mesh generation comprises triangulating or tetrahedralizing the third sample parameters.

27. The method of claim 18, wherein the sample characteristic comprises a cardiac arrhythmia indicator.

28. The method of claim 18, wherein the sample characteristic comprises a rotor or a focal impulse.

29. A method, comprising:
collecting a first electrical signal from each of a first plurality of locations in a sample at a first time;
processing the first electrical signals to obtain a first sample parameter for each of the first plurality of locations in the sample at the first time;
collecting a second electrical signal from each of a second plurality of locations in a sample at a second time;
wherein the first plurality of locations and the second plurality of locations have at least one location in common;

processing the second electrical signals to obtain a second sample parameter for each of the second plurality of locations in the sample at the second time;

comparing the second sample parameters to the first sample parameters to obtain a third sample parameter at each of the first plurality of locations and the second plurality of locations; and processing the third sample parameters to determine a sample characteristic, wherein:
the first sample parameter comprises frequencies, phases or a combination thereof at each of the first plurality of locations;
the second sample parameter comprises frequencies, phases, or a combination thereof at each of the second plurality of locations;
the third sample parameter comprises frequencies and phases at each of the first plurality of locations and the second plurality of locations;
or a combination thereof.

30. The method of claim 29, wherein the sample comprises an organ.

31. The method of claim 29, wherein the organ comprises the heart.

32. The method of claim 29, wherein the first electrical signal, the second electrical signal, or a combination thereof comprises voltage.

33. The method of claim 29, wherein processing the first electrical signals, the second electrical signals, or a combination thereof comprises applying a transform function, a trigonometric function, or a combination thereof.

34. The method of claim 29, wherein processing the first electrical signals, the second electrical signals, or a combination thereof comprises applying a Fourier transform and an arctangent function.

35. The method of claim 29, wherein comparing the second sample parameters and the first sample parameters comprises applying a correction function to the second sample parameters to obtain the third sample parameters, wherein the correction function is determined based on a phase difference between the first sample parameter and the second sample parameter at the location in common between the first plurality of location and the second plurality of locations.

36. The method of claim 29, wherein processing the third sample parameters comprises mesh generation of the third sample parameters to obtain a sample characteristic.

37. The method of claim 36, wherein the mesh generation comprises triangulating or tetrahedralizing the third sample parameters.

38. The method of claim 29, wherein the sample characteristic comprises a cardiac arrhythmia indicator.

39. The method of claim 29, wherein the sample characteristic comprises a rotor or a focal impulse.

* * * * *